(12) United States Patent
Koppenhofer

(10) Patent No.: US 7,641,913 B2
(45) Date of Patent: Jan. 5, 2010

(54) **ISOLATED SPECIES OF *STEINERNEMATID* NEMATODE AND METHODS OF WHITE GRUB CONTROL THEREWITH**

(75) Inventor: Albrecht M. Koppenhofer, Lawrenceville, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 935 days.

(21) Appl. No.: 10/964,192

(22) Filed: Oct. 12, 2004

(65) Prior Publication Data

US 2005/0048037 A1    Mar. 3, 2005

Related U.S. Application Data

(62) Division of application No. 10/229,750, filed on Aug. 28, 2002, now Pat. No. 7,011,837.

(60) Provisional application No. 60/315,335, filed on Aug. 29, 2001.

(51) Int. Cl.
    *A01N 63/00*    (2006.01)
(52) U.S. Cl. ............... 424/406; 424/265.1; 424/405; 119/6.7; 514/341
(58) Field of Classification Search ............... None
    See application file for complete search history.

(56) References Cited

U.S. PATENT DOCUMENTS

| | | | |
|---|---|---|---|
| 4,753,799 A | 6/1988 | Nelsen et al. | |
| 5,405,961 A * | 4/1995 | Nanjo et al. | 544/243 |
| 5,674,516 A | 10/1997 | Raulston et al. | |
| 5,932,237 A | 8/1999 | Raulston et al. | |
| 6,184,434 B1 | 2/2001 | Raulston et al. | |
| 6,399,542 B1 * | 6/2002 | Henmi et al. | 504/344 |
| 6,759,407 B2 * | 7/2004 | Goebel et al. | 514/226.8 |

FOREIGN PATENT DOCUMENTS

WO    WO 91/06642    5/1991

OTHER PUBLICATIONS

Koppenhofer et al Synergism of Entomopathogenic Nematodes and Imidacloprid—Biological Control (2000), 19 (3), 245-251.*

* cited by examiner

*Primary Examiner*—Neil Levy
(74) *Attorney, Agent, or Firm*—Porzio, Bromberg & Newman P.C.

(57) ABSTRACT

An isolated *Steinernematid* nematode of the species *Steinernema scarabaei* (ATCC accession No. PTA-6988) is provided which is entomopathogenic to the larvae of scarab beetles, e.g., Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga*spp). A biopesticide composition is provided which comprises an insecticidally effective amount of *Steinernema scarabaei*. Biopesticide compositions are described which, in addition to *Steinernema scarabaei*, further comprise at least one neonicotinoid insecticide, e.g., imidacloprid. Methods are provided for controlling the larvae of at least one species of scarab beetle comprising applying a biopesticide composition to the locus of the larvae wherein the composition comprises an insecticidally effective amount of an isolated entomopathogenic nematode of the species *Steinernema scarabaei*.

2 Claims, 1 Drawing Sheet

ISOLATED SPECIES OF *STEINERNEMATID* NEMATODE AND METHODS OF WHITE GRUB CONTROL THEREWITH

This application is a divisional of patent application Ser. No. 10/229,750, filed Aug. 28, 2002, now U.S. Pat. No. 7,011, 837 which claims priority under 35 U.S.C. 119 (e) from U.S. provisional application Ser. No. 60/315,335, which was filed Aug. 29, 2001.

FIELD OF THE INVENTION

This invention relates to a novel entomopathogenic nematode of the genus *Steinernema*, which is effective as a biopesticide for the control of insects, particularly the larvae of scarab beetles such as Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga* spp.). Biopesticide compositions are provided which comprise an insecticidally effective amount of an isolated nematode of the species *Steinernema scarabaei* (ATCC accession No. PTA-6988). Methods are provided for controlling the larvae of scarab beetles.

BACKGROUND OF THE INVENTION

White grubs, the root-feeding larvae of scarab beetles (Coleoptera: Scarabaeidae), are important pests of turf and pasture grasses, ornamental plants, and numerous crops around the world. At least 10 species cause significant damage to turfgrasses in North America. In fact, a complex of primarily introduced white grub species are the major turfgrass insect pests. Among these, the Japanese beetle, *Popillia japonica*, has until recently been regarded as the key species, but other white grub species are becoming more important. These other species include the oriental beetle, *Exomala orientalis*, the European chafer, *Rhizotrogus majalis*, and the Asiatic garden beetle, *Maladera castanea*. Surveys have indicated that the oriental beetle has become the most important white grub species. The subterranean habit of the larvae of scarab beetles makes them some of the most difficult to control insect pests.

Chemical insecticides are the primary means of controlling white grubs. Organophosphate and carbamate insecticides are used for curative control of white grubs, however, toxicological and environmental problems related to their application have already or will soon lead to the loss of registrations of many compounds or uses of these compounds. The implementation of the Food Quality Protection Act of 1996 in the United States, for example, is responsible for these increasing restrictions on the use of organophosphates (and potentially also carbamates). While new types of insecticides with better toxicological and environmental characteristics (e.g., neonicotinoids, insect growth regulators) are becoming increasingly available for white grub control, these compounds generally have to be applied preventively because their efficacy declines with advancing white grub development. Because white grub outbreaks are generally difficult to predict, this preventive approach often results in the treatment of large areas that may only need partial or no treatment. This not only increases the cost of white grub management, but also may have unintended environmental consequences such as long-term suppression of beneficial insects.

Entomopathogenic nematodes (Heterorhabditidae and Steinernematidae) offer an environmentally safe 'biopesticide' alternative to chemical insecticides for the control of white grubs. These nematodes possess most of the characteristics of an ideal biological control agent for insects. Koppenhöfer, In: Lacey and Kaya (eds.), Field Manual of Techniques in Invertebrate Pathology, Kluwer Academic Publishers, pp. 283-301 (2000). Nematodes have been studied quite extensively as white grub control agents. However, overall the level of white grub control has been often inconsistent and unsatisfactory. Klein, In: Nematodes and the biological control of insect pests, CSIRO, East Melbourne, pp. 49-58 (1993). A reason for this inconsistency is the difference in nematode susceptibility among different white grub species. Thus, important white grub pests such as the European chafer or the oriental beetle, for example, are very resistant to infection by some of the previously used nematode species.

SUMMARY OF THE INVENTION

The present invention is directed to an isolated entomopathogenic nematode of the species *Steinernema scarabaei* (ATCC accession No. PTA-6988) which is an effective biopesticide agent for the control of insects, particularly the larvae of scarab beetles such as the Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga* spp.).

The invention is further directed to an isolated and substantially homogenous population of a nematode of the species *Steinernema scarabaei*.

A biopesticide composition is provided which comprises an insecticidally effective amount of an isolated nematode of the species *Steinernema scarabaei*.

A biopesticide composition is further provided which comprises an insecticidally effective amount of an isolated nematode of the species *Steinernema scarabaei*—and—at least one neonicotinoid insecticide, e.g., imidacloprid.

An object of the invention is to provide a method for controlling the larvae of scarab beetles (white grubs) comprising applying a biopesticide composition to the locus of the larvae wherein the composition comprises an insecticidally effective amount of an isolated entomopathogenic nematode of the species *Steinernema scarabaei*.

A further object of the invention is to provide a method for controlling the larvae of scarab beetles (white grubs) comprising applying a biopesticide composition to the locus of the larvae wherein the composition comprises an insecticidally effective amount of an isolated entomopathogenic nematode of the species *Steinernema scarabaei*—and—at least one neonicotinoid insecticide, e.g., imidacloprid.

DETAILED DESCRIPTION OF THE INVENTION

Figure 1:
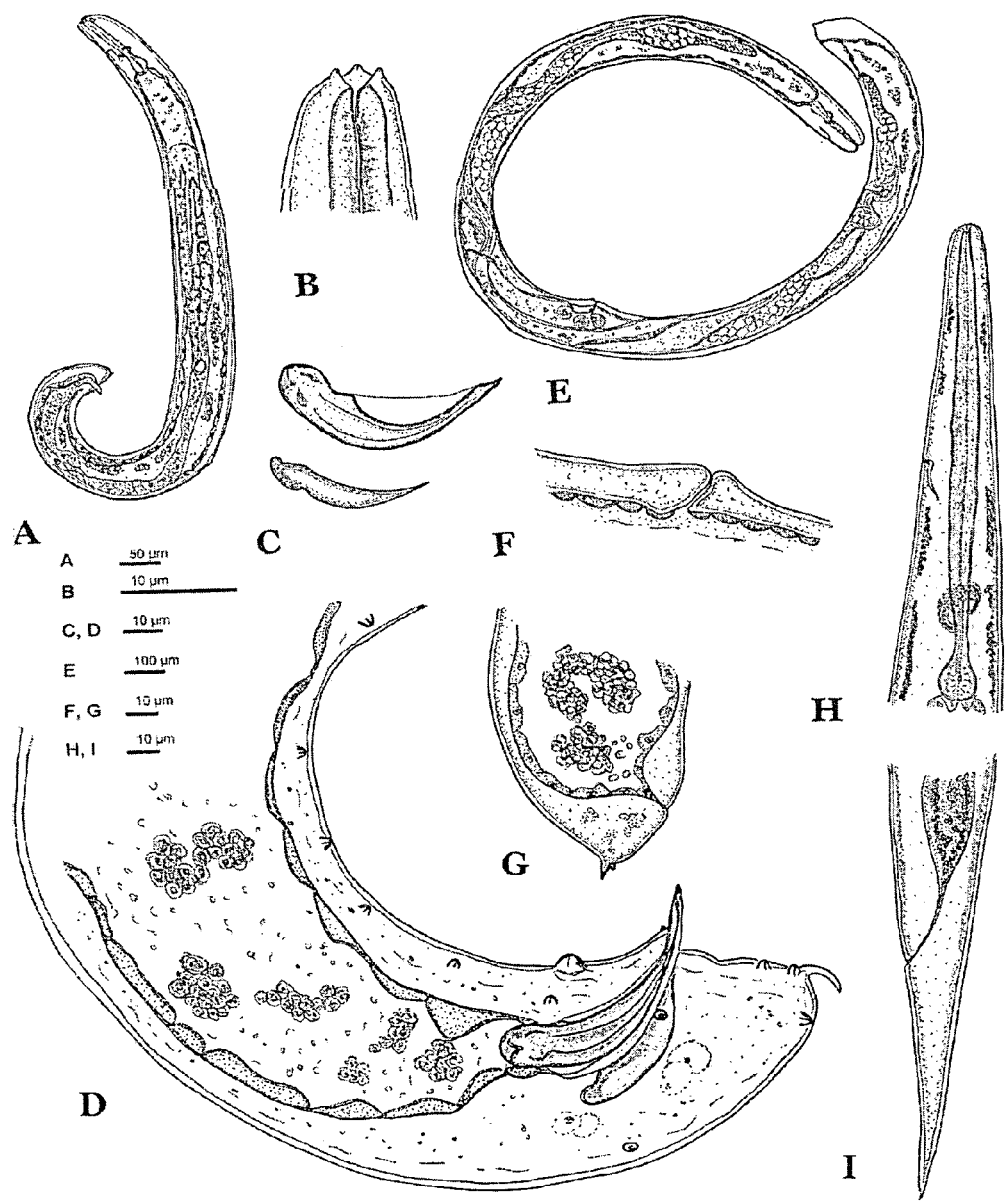
FIG. 1 displays the isolated and characterized *Steinernema* species of the present invention; wherein, view A shows an entire body of first generation male; view B shows an anterior end (lateral view) of first generation male; view C shows spicule and gubernaculum of first generation male; view D shows a tail (lateral view) of first generation male; view E shows an entire body of first generation female; view F shows a vulva (lateral view) of a first generation female; view G shows a tail (lateral view) of a first generation female; view H shows an anterior end (lateral view) of third-stage infective juvenile; and, view I shows a tail (lateral view) of a third-stage infective juvenile.

Unless defined otherwise, all technical and scientific terms used herein have the same meaning as is commonly understood by one of skill in the art to which this invention belongs. All publications and patents referred to herein are incorporated by reference.

The term "entomopathogenic nematode" is used in the art to refer to the nematode's ability to quickly kill hosts facilitated by their mutualistic (symbiotic) association with bacteria. The stage that survives outside of a host is the non-feeding, non-developing third stage infective juvenile (IJ) or dauer juvenile. The infective juveniles carry cells of their bacterial symbiont in their intestines. After locating a suitable host, the infective juveniles invade it through natural openings (mouth, spiracles, anus) or thin areas of the host's cuticle and penetrate into the host hemocoel. The infective juveniles release their symbiotic bacteria that propagate, kill the host by septicemia, and metabolize its tissues. The nematodes start developing and feed on the bacteria and metabolized host tissues, and go through 1-3 generations, until a new generation of infective juveniles emerges from the depleted host cadaver.

An "isolated" *Steinernematid* nematode species, for example, as used herein refers the characterized species of the present invention described herein, *Steinernema scarabaei* (American Type Culture Collection (ATCC, Manassas, Va. 20108-USA)accession No. 6988) which is artificially separated and particularly cultivated, propagated and/or stored apart from its natural soil environment. Although the species name is not yet official, the isolated and characterized *Steinernema* species of the present invention described herein will be referred to as *Steinernema scarabaei*.

An "insecticidally effective amount" is defined herein as that quantity that results in a significant mortality rate of the target insects under standard laboratory conditions, for example, as demonstrated in the Examples and Tables presented herein—or—a 5 ft.×5 ft. field test locus, for example, when compared to a control or untreated group. An insecticidally effective amount may refer to an approximate number of *Steinernema scarabaei* infective juveniles (U) per hectare (ha), for example, that may be necessary to control the larvae of at least one species of scarab beetle, e.g., Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga* spp.).

An isolated and substantially homogenous population of a nematode of the species *Steinernema scarabaei* refers to a population which is artificially separated and preferably stored apart from its natural soil environment and which sample is particularly suitable for cultivation or seeding propagation or production of the species.

*Steinernema scarabaei* of the current invention is demonstrated to show unusually high pathogenicity toward particular beetle grubs (further described infra). Moreover the size, morphological features, and behavior of the infective juvenile stage of the species is distinct (further described infra) from entomopathogenic nematode species currently known. The *Steinernema scarabaei* of the current invention does not cross-hybridize or inter-breed with any other known species.

Commercial Utility

This invention relates to a novel entomopathogenic nematode of the genus *Steinernema*, which is effective as a biopesticide for the control of insects, and particularly the larvae of scarab beetles (white grubs), including but not limited to, the Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga* spp.). A significantly valuable aspect of the current invention is the pathogenicity of *Steinernema scarabaei* to white grubs and demonstrated efficacy, particularly in controlling the larvae of the Japanese beetle. This provides for commercial embodiments of compositions and methods of use for controlling the larvae of these and other scarab beetles. The nematode may be applied for the control of economically important insects on turf and pasture grasses, ornamental plants, or any crop that may be damaged by these pests. When applied to the locus of the target insects described herein, for example, *Steinernema scarabaei* of the invention will provide very good to complete suppression or control of the target insect population.

The *Steinernema scarabaei* of the present invention is a pathogen highly adapted to the larvae of scarab beetles as an integral element of its own reproductive cycle. In fact, as demonstrated in the Examples and Tables presented herein, the pathogenicity of the *Steinernema* species of this invention herein is significantly greater, for example, against the larvae of Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga* spp.) than that of other presently known nematodes species. The superior insecticidal properties of *Steinernema scarabaei* against the white grub larvae of Japanese beetles, for example, is apparent at low application rates under field conditions. The insecticidal efficacy of *Steinernema scarabaei* against larvae of the northern masked chafer under field conditions, for example, is significantly greater than that of other known nematode species. The insecticidal efficacy of *Steinernema scarabaei* against the larvae of the oriental beetle, the European chafer, and the Asiatic garden beetle, is also several times greater than other nematode species.

Example II demonstrates *Steinernema scarabaei* infectivity compared to other nematode species/isolates. The insecticidal efficacy of *Steinernema scarabaei* against the larvae of the oriental beetle, the Asiatic garden beetle, and the European chafer, for example, greatly outperforms any other nematode isolate. Overall, as shown in Table 1, *Steinernema scarabaei* is the most pathogenic nematode species/isolate under the laboratory conditions used.

Example III further illustrates the high pathogenicity of *Steinernema scarabaei*. As demonstrated, only 17.9 infective juveniles (IJs) per larva are necessary to kill 50% of oriental beetle larvae (35.2 are necessary to kill 90%). Japanese beetle larvae are even more susceptible and only 10.9 IJs per larva are necessary to achieve 50% mortality (22.3 are necessary to achieve 90% mortality). LC50 (LC90) is a concentration of *Steinernema scarabaei* that kills 50 (90) percent of a population.

Example IV provides characteristics of the infection and reproductive biology of the species and further shows the high pathogenicity (85-98% mortality) against the larvae of the oriental beetle. All dosages of *Steinernema scarabaei* caused high oriental beetle mortality (85-98%) (Table 3).

Example V demonstrates the insecticidal efficacy of *Steinernema scarabaei*, particularly against Japanese beetle larvae, wherein for example at the extraordinarily low rate of 0.3125×10$^9$ infective juveniles per ha, *Steinernema scarabaei* provides 90% control. Furthermore, *Steinernema scarabaei* causes a 2-4 times higher mortality than any other nematode isolate in the oriental beetle larvae. *Steinernema scarabaei* is also demonstrated to be effective against the Asiatic garden beetle larvae (see also, Example VII) and larvae of the European chafer.

*Steinernema scarabaei* is shown in Example VI to provide complete control (100%) against Japanese beetle larvae within 14 days, even at the low-end application rate of 1×10$^9$ infective juvenile nematodes per ha, (Table 5) for example. *Steinernema scarabaei* is also demonstrated to provide excellent control (80-93%) of oriental beetle larvae within 14 days even at the lower application rate. The high infection rate of Japanese beetle and oriental beetle larvae by *Steinernema scarabaei*, for example, indicates that this newly isolated and characterized species can not only provide excellent short term control of scarab larvae but also has a high potential for long-term suppression due to efficient reproduction in its hosts.

*Steinernema scarabaei* is also shown in Example VIII to provide control (e.g., 84%) against the northern masked chafer under field conditions.

Example IX demonstrates that the combination of *Steinernema scarabaei* with the neonicotinoid insecticide imidacloprid results in a synergistic enhancement of the mortality of the larvae of scarab beetles compared to imidacloprid alone or *Steinernema scarabaei* alone (Table 9). The interactions are synergistic in all combinations tested. Imidacloprid alone did not cause significant mortality.

Examples X, XI and XII are directed toward the *Steinernema scarabaei* taxonomic description of Females, Males, and Third stage infective juveniles, respectively.

Morphological Features

Morphological data indicate that *Steinernema scarabaei* belongs to the group of species commonly know as the *S. glaseri*-group. *Steinernema scarabaei* can be separated from other *Steinernema* spp. by several characteristics. The average IJ body length of the *Steinernema scarabaei* described herein is about 918 µm, and ranges from about 890 µm to about 959 µm. The average maximum body width of each *Steinernema scarabaei* single specimen is about 31 µm (the range of diversity is from about 25 µm to about 37 µm).

The new species can be distinguished from most of the taxa that belong to the *S. glaseri*-group, for example, by the average body length of the IJs, which is shorter than that of *S. arenarium, S. glaseri, S. longicaudum, S. puertoricense* and *S. cubanum*. The nerve ring of the IJ of the *Steinernema scarabaei* described herein is more posteriorly located (about 120 µm from the anterior end of the nematode) than that of *S. feltiae* (about 99 µm from the anterior end of the nematode) and *S. kraussei* (about 107 µm from the anterior end of the nematode).

Females of *Steinernema scarabaei* can be distinguished from *S. arenarium, S. glaseri, S. longicaudum, S. puertoricense* and *S. cubanum*, for example, by the morphology of the vulval lips (slightly protruding) and tail (conoid in first generation female, blunt-conoid in second generation females). Additionally, the presence of a tail papilla (located at the base of the mucro) in the females of *Steinernema scarabaei* is a feature that is unique to this species and has not been reported in any previously described *Steinernema* spp.

The IJs of the new species resemble most closely *S. karii*. Some key-diagnostic morphological characters of this stage (i.e. total body length, tail length, D % and E %) are very similar in these two species. However *Steinernema scarabaei* can be distinguished from *S. karii*, for example, by the morphology of the male spicules and gubernaculum and the number and arrangement of the genital papillae. The size of the spicules of *Steinernema scarabaei* is much shorter (having an average length of about 75 µm (the range of diversity is from about 67 µm to about 83 µm)) than those of *S. karii* (average: 83 µm), but longer than that of *S. cubanum* (average: 58 µm) and *S. kushidai* (average: 63 µm). The size of the gubernaculum of the new species is shorter (having an average length of about 43.5 µm (the range of diversity is from about 36 µm to about 50 µm) than that of *S. arenarium* (average: 53 µm) and *S. glaseri* (average: 55 µm), but longer than that of *S. cubanum* (average: 39 µm). The arrangement of *Steinernema scarabaei* genital papillae is different from that of *S. glaseri, S. arenarium, S. puertoricense, S. cubanum* and *S. kushidai*. Male *Steinernema scarabaei* have from about 23 to about 25 genital papillae (usually 11-12 pairs and usually one single) arranged usually as follows: 6 precloacal subventral pairs, one precloacal lateral pair, one single ventral precloacal papilla (located between precloacal pairs 5 and 6), one adcloacal (or postcloacal in some specimen) pair, one postcloacal subventral pair, postcloacal subdorsal pair, and one postcloacal terminal pair near the tail tip. An additional pair of papillae may be present at the base of the cloacal cone in around 40% of first generation males.

Nucleic acid sequence data derived from Large Subunit of ribosomal DNA (LSU rDNA), for example, from the *Steinernema scarabaei* described herein, when compared to a library of over 20 species, moreover indicates that the *Steinernema scarabaei* of the invention is a distinct species. Phylogenetic parsimony analysis of these sequences indicates *Steinernema scarabaei* is more closely related, for example, to *S. karii* as well as a new *Steinernema* species from California. However, when compared to these two species, *Steinernema scarabaei* presents 19 autapomorphies (unique characters). Additionally and when compared to the "*feltiae/kraussei/oregonense*" group, this new species differs in more than 30 autapomorphies. Finally, in cross-hybridization tests *Steinernema scarabaei* does not interbreed with any of the morphologically similar species. Reproductive compatibility of the new species was tested using the following *Steinernema* spp: *Steinernema glaseri* (Steiner), *S. puertoricense* Román and Figueroa, *S. longicaudum* Shen and Wang (USA isolate), *S. karii* Waturu, Hunt and Reid, *S. kushidai* Mamiya, and *S. arenarium* (Artyukhovsky).

The infective juvenile *Steinernema scarabaei* described herein can be distinguished from other *Steinernema* spp. by morphological features, which include but are not limited to, for example, the position of the excretory pore, which is about 77 µm from the anterior end of the nematode (the range of diversity is from about 72 µm to about 82 µm from the anterior end of the nematode). This feature, the excretory pore, is more posteriorly located in the *Steinernema scarabaei* of the present invention than that of *S. oregonense* (about 66 µm from the anterior end of the nematode), *S. feltiae* (about 62 µm from the anterior end of the nematode) and *S. kraussei* (about 63 µm from the anterior end of the nematode). First-generation males of *Steinernema scarabaei* of the invention can also be distinguished from *S. kraussei*, for example, by having larger spicules. First-generation male *Steinernema scarabaei* described herein display spicules having an average length of about 75 µm (the range of diversity is from about 67 µm to about 83 µm); whereas, first-generation male *S. kraussei* display spicules having an average length of about 49 µm. First-generation males of *Steinernema scarabaei* of the invention can also be distinguished from *S. kraussei* by having larger gubernaculum. First-generation male *Steinernema scarabaei* described herein display gubernaculum having an average length of about 43.5 µm (the range of diversity is from about 36 µm to about 50 µm); whereas, first-generation male *S. kraussei* display gubernaculum having an average length of about 33 µm. The *Steinernema scarabaei* described herein IJ D %-value (distance from anterior end to excretory pore divided by esophagus length×100) of is about 60 (the range of diversity is from about 50 to about 110). Males of the new species can be distinguished from *S. kraussei* by the arrangement of the male genital papillae, and by the absence of a mucro in the tail of the second generation males. IJs of *Steinernema scarabaei* can be separated from *S. kraussei* by the value of D % (average: 60 vs. 47 in *S. kraussei*) and E % (average: 100 vs. 80 in *S. kraussei*). First generation females of the novel *Steinernema scarabaei* can be distinguished from all other *Steinernema* spp. by the presence of a tail papilla (located at the base of the mucro) in first generation females that is unique to this species and has not been reported from any other described *Steinernema* spp.

It is noted herein however that a shift in the average as well as the ranges recited herein may be accomplished by rearing the nematodes under other than normal conditions (e.g. a bad host or overcrowding).

Production

The *Steinernema scarabaei*, of the present invention may be isolated from its natural environment in larvae of, for example, Japanese beetles (*Popillia japonica*) or oriental beetle (*Exomala* (=*Anomala*) *orientalis*) from the soil of turfgrass, for example. The nematode has been isolated, for example, in turfgrass areas in the northeastern United Sates. Particularly, the species of the invention can be isolated from turfgrass soil in the state of New Jersey, for example, from larvae of the Japanese beetle and the oriental beetle, and from soil samples using Japanese beetle and oriental beetle larvae as baits. The nematode may be isolated from the field by collecting infected-looking white grubs from the soil under turfgrass areas and placing them on emergence traps (known in the art as White traps) to collect any emerging progeny nematodes from the grub cadavers. White, Science, 665:302-303, (1929). Soil samples may also be taken from the field, for example, and baited by adding grubs as baits for the nematodes. Then grubs that become infected in the soil cups may be placed onto emergence traps. See Example I.

Production of the nematode may be accomplished using in vivo or in vitro techniques known in the art. As described in the Examples herein, *Steinernema scarabaei* may be initially recovered from infected scarab larvae recovered from the field or from soil samples using scarab larvae as baits. Following isolation from the environment, the nematodes may then be reared in vivo in susceptible host insects such Japanese or oriental beetle larvae (also in late instar larvae of the greater wax moth, *Galleria mellonella*) as illustrated in the Examples. In accordance with preferred methods of commercial production, for example, the nematodes may also be produced on a large scale using in vitro rearing techniques. See, e.g., Shapiro-Ilan, D. I., et al., *Production Technology for Entomopathogenic Nematodes and their Bacterial Symbionts*, J. Ind. Microbiol. Biotechnol., 28(3):137-46 (2002); Ehlers, R. U., *Mass Production of Entomopathogenic Nematodes for Plant Protection*, Appl. Microbiol. Biotechnol., 56(5-6):623-33 (2001); Friedman, et al., *Mass Production in Liquid Culture of Insect-killing Nematodes*, U.S. Pat. No. 5,023,183, issued Jun. 11, 1991. In accordance with either in vivo or in vitro techniques, the nematodes may be subsequently isolated and collected in pure or substantially pure form. A variety of formulations are available moreover to facilitate nematode storage. Shapiro-Ilan D I, et al., *Production Technology for Entomopathogenic Nematodes and their Bacterial Symbionts*, J. Ind. Microbiol. Biotechnol., 28(3): 137-46 (2002).

Biopesticide Compositions

Suitable formulations for commercial insecticidal biopesticide compositions are prepared from *Steinernema scarabaei* nematodes isolated from the environment, particularly in vitro cultivated populations of the nematodes, preferably substantially pure *Steinernema scarabaei* nematodes. Because of the moisture requirements of these nematodes for continued viability and infectivity, the nematodes are advantageously applied in combination with water and/or another suitable inert carrier or vehicle as known in the art, which carrier is optionally substantially biologically pure. The term "substantially biologically pure inert carrier" is defined herein as an inert carrier having significantly fewer naturally occurring microorganisms relative to the environment. A preferred biopesticide composition comprises an insecticidally effective amount of an isolated entomopathogenic nematode of the species *Steinernema scarabaei* and a carrier. The carrier may be water. Formulations may be produced that are stable for storage and, depending upon the composition, nematode viability can be maintained, for example, one year or more with refrigeration. As a practical matter, to facilitate handling and transport of the *Steinernema scarabaei* biopesticide compositions, and to prevent desiccation, the formulations of the nematode should be enclosed within a container such as a drum, jug, flask, or plastic bag as in known in the art.

A well-known variety of formulations are available to facilitate nematode application. See, e.g., Shapiro-Ilan, D. I., et al., *Production Technology for Entomopathogenic Nematodes and their Bacterial Symbionts*, J. Ind. Microbiol. Biotechnol., 28(3):137-46 (2002). Of particular interest are formulations employing water as a carrier, with a population of the nematodes suspended therein. In an alternative embodiment the carrier may be, or the biopesticide composition may further comprise, a solid phase carrier including but not limited to encapsulating agents, upon or within which the nematodes can be immobilized. Suitable solid phase carriers of this type include but are not limited to hydrogel agents such as alginate gels, wheat-gluten matrices, starch matrices, wheat-bran bait pellets, clay particles, polyacrylamide gels, or synthetic polymers as are known in the art, activated charcoal, peat, polyurethane sponge, vermiculite, and/or water dispersible granules (WDG). WDG formulation may be used, for example, in which the nematodes enter a partially anhydrobic state allowing for them to survive for relatively long periods of time. See, e.g., Georgis, et al., *Formulation of Entomopathogenic Nematodes*, In: Hall, F. R, et al., Eds., Biorational Pest Control Agents: Formulation and Delivery, American Chemical Society, Washington D.C., 197-205 (1995). Formulations of alginate gels containing the nematodes provide the added benefit of enhanced viability after storage, while allowing subsequent conversion to an aqueous liquid by dissolution of the alginate with sodium citrate. When the carrier is other than water, sufficient moisture should be provided to ensure viability and infectivity of the nematodes. Besides the active agent itself, other additives and adjuncts may be formulated into the compositions of the invention. Examples of these include nutrients, humectants, feeding stimulants (phagostimulants), UV protectants, inert fillers, and dispersants. Humectant materials include but are not limited to glycerol, sugars such as sucrose, invert emulsions, and cellulose ethers. See, e.g., Nelson, et al., U.S. Pat. No.

4,701,326; Georgis, R., *Formulation and Application Technology*, In: Gaugler, et al., Eds., *Entomopathogenic Nematodes in Biological Control*, CRC Press, Boca Raton, Fla., 173-194 (1990); Raulston, et al., U.S. Pat. No. 6,184,434.

Methods of Use

An insecticidally effective amount of the *Steinernema scarabaei* is applied to the locus of, or in the vicinity of, insects to be controlled. An insecticidally effective amount for example may refer to an approximate number of *Steinernema scarabaei* infective juveniles (IJ) per hectare (ha) that may be necessary to control the larvae of at least one species of scarab beetle, e.g., Japanese beetle (*Popillia japonica*), oriental beetles (*Exomala* (=*Anomala*) *orientalis*), European chafer (*Rhizotrogus majalis*), Asiatic garden beetle (*Maladera castanea*), masked chafers (*Cyclocephala* spp.), and May/June beetles (*Phyllophaga* spp.). The actual effective amount may be readily determined by the practitioner skilled in the art, and may vary with the species of pest, stage of larval development, the type of vehicle or carrier, the period of treatment, environmental conditions (especially moisture), and other related factors. Without being limited thereto, in accordance with embodiments of the invention, the *Steinernema scarabaei* nematodes are generally applied at a concentration of—from about $0.25 \times 10^9$ infective juveniles per hectare in the field—to about $5 \times 10^9$ infective juveniles per hectare in the field. However, less (or more) can be used depending upon the compositions, including the combination of *Steinernema scarabaei* with imidacloprid, for example; and formulations employed, as well as conditions, locus, identity, and population of the target insects.

In accordance with an embodiment for use in areas employing irrigation, the nematodes may be admixed with irrigation water prior to or at the time of irrigation, effectively distributing the nematodes across the field.

A preferred method of the invention is that of controlling the larvae of at least one species of scarab beetle comprising applying a biopesticide composition of the invention to the locus of the larvae to be controlled and wherein the composition comprises an insecticidally effective amount of an isolated entomopathogenic nematode of the species *Steinernema scarabaei*.

The field (locus) rate of application of the newly isolated and characterized species, *Steinernema scarabaei*, for controlling the larvae of scarab beetles, particularly the Japanese beetle, oriental beetle, European chafer, Asiatic garden beetle and/or masked chafer species, for example, ranges generally from about $0.25 \times 10^9$ infective juveniles (IJ) per hectare (ha) to about $5 \times 10^9$ IJ per ha. A preferred range of *Steinernema scarabaei* application is from about $1 \times 10^9$ IJ per ha to about $2.5 \times 10^9$ IJ per ha. This preferred range is also a preferred range of rate of *Steinernema scarabaei* application to control the larvae of scarab beetles, particularly the Japanese beetle, oriental beetle, European chafer, Asiatic garden beetle and masked chafer species, for example, in turfgrass. However, lower rates of *Steinernema scarabaei* application may be used, for example, from about $0.25 \times 10^9$ IJ per ha to about $1 \times 10^9$ IJ per ha, as well as higher rates, for example, from about $2.5 \times 10^9$ IJ per ha to about $5 \times 10^9$ IJ per ha, may be successfully employed for controlling the larvae of scarab beetles as described herein. These rates of application are intended to be within the scope of the claims appended hereto.

Example V demonstrates the insecticidal efficacy of *Steinernema scarabaei*, particularly against Japanese beetle larvae, wherein for example at the extraordinarily low rate of $0.3125 \times 10^9$ infective juveniles per ha, *Steinernema scarabaei* provides 90% control. Which rate will provide acceptable control will depend on a number factors including white grub species to be controlled, crop system and management practices, environmental conditions, degree of control needed, and speed of control required.

In order to maximize the efficacy of the insecticidal activity of *Steinernema scarabaei*, and the biopesticide compositions/formulations described herein, because *Steinernema scarabaei* actively seek out and then penetrate and parasitize the target insects, the application of the nematodes and compositions to the soil should be properly timed to the presence of scarab beetle larvae, for example, in the soil when they, as a group population, are most susceptible.

Combinations

Combining nematodes with synergists may be a strategy that could permit cost-effective use of nematodes, even under stringent situations. An efficient combination with wide applicability is that of *Steinernema scarabaei* and the neonicotinoid insecticide imidacloprid. Koppenhöfer, et al., for example, have shown that combined applications of the scarab-adapted entomopathogenic nematodes *S. glaseri* or *H. bacteriophora* and imidacloprid resulted in synergistic mortality of third-instar white grubs. See, Journal of Economic Entomology, 91:618-623 (1998); Biological Control, 19:245-251 (2000). This interaction was observed over a range of imidacloprid rates, with simultaneous or delayed nematode application, and for five scarab species (*P. japonica*, *E. orientalis*, and the masked chafers, *Cyclocephala hirta*, *C. pasadenae*, and *C. borealis*) with different degrees of nematode susceptibility. Koppenhöfer, et al., further showed that the major factor responsible for this synergistic interaction is the general disruption of normal nerve function due to imidacloprid, resulting in reduced defensive activity of the grubs which facilitates host attachment by infective juvenile nematodes and subsequent infection. Entomologia Experimentalis et Applicata, 94:283-293 (2000). In fact the major factor responsible for synergistic interactions between imidacloprid and entomopathogenic nematodes appears to be the general disruption of normal nerve function due to imidacloprid resulting in drastically reduced grub activity. Grooming and evasive behavior in response to nematode attack was also reduced in imidacloprid-treated grubs.

Chloronicotinyl Neonicotinoid Compounds

Any neonicotinoid compound having insecticidal properties against the larvae of scarab beetles may be used in combination with the isolated nematode species *Steinernema scarabaei* of the present invention in methods of the invention to control the larvae of scarab (white grubs including, but not limited to the larvae of Japanese beetles, European chafers, Asiatic garden beetles, oriental beetles, May/June beetles, and masked chafers) beetles and to provide compositions of the present invention. A preferred biopesticide composition of the present invention comprises an insecticidally effective amount of an isolated entomopathogenic nematode of the species *Steinernema scarabaei*, at least one neonicotinoid insecticide, and a carrier. However, although intended to be within the scope of the claims appended hereto, due to the synergistic activity of *Steinernema scarabaei* in combination with imidacloprid, for example, the amount of neonicotinoid insecticide, in and of itself, employed within the biopesticide compositions described herein need not necessarily be of an "insecticidally effective amount".

Example neonicotinoid compounds for use in the present invention include but are not limited to, for example, imidacloprid [1-(6-chloro-3-pyridylmethyl)-N-nitroimidazolidin-2-ylideneamine, CAS 138261-41-3], thiamethoxam, and acetamiprid. See, e.g., Maienfisch P., et al., Chemistry and biology of thiamethoxam: a second generation neonicotinoid, Pest Manag Sci., 57(10):906-13 (2001); Tomizawa M., et al., Structure and diversity of insect nicotinic acetylcholine receptors, Pest Manag Sci., 57(10):914-22 (2001).

A method of the invention is that of controlling the larvae of at least one species of scarab beetle comprising applying a biopesticide composition of the invention to the locus of the larvae to be controlled and wherein the composition comprises an insecticidally effective amount of an isolated entomopathogenic nematode of the species *Steinernema scarabaei* and an insecticidally effective amount of at least one neonicotinoid insecticide, e.g., imidacloprid.

Methods of Use of Combinations

The field rate of application of compositions which comprise the neonicotinoid compound imidacloprid, in combination with the newly isolated and characterized species, *Steinernema scarabaei*, for controlling the larvae of scarab beetles, particularly the Japanese beetle, oriental beetle, European chafer, Asiatic garden beetle and masked chafers, for example, ranges generally from about 25 grams (g) imidacloprid per ha to about 400 g imidacloprid per ha. See, e.g., Koppenhöfer A. M., et al., *Comparison of neonicotinoid insecticides as synergists for entomopathogenic nematodes*, Biol. Contr. 24, 90-97 (2002). Accordingly, compositions which comprise the isolated nematode species *Steinernema scarabaei* and imidacloprid, as active ingredients, allow for an effective field rate of application generally from about $0.25 \times 10^9$ IJ *Steinernema scarabaei* per hectare (ha) to about $5 \times 10^9$ IJ *Steinernema scarabaei* per ha and from about 25 grams (g) imidacloprid per ha to about 400 g imidacloprid per ha, respectively. Preferred compositions which comprise the isolated nematode species *Steinernema scarabaei* and imidacloprid, as active ingredients, allow for an effective field rate of application from about $0.25 \times 10^9$ IJ *Steinernema scarabaei* per hectare (ha) to about $2.5 \times 10^9$ IJ *Steinernema scarabaei* per ha and from about 25 grams (g) imidacloprid per ha to about 200 g imidacloprid per ha, respectively. Further compositions which comprise the isolated nematode species *Steinernema scarabaei* and imidacloprid, as active ingredients, allow for an effective field rate of application from about $0.5 \times 10^9$ IJ *Steinernema scarabaei* per hectare (ha) to about $1.5 \times 10^9$ IJ *Steinernema scarabaei* per ha and from about 50 grams (g) imidacloprid per ha to about 150 g imidacloprid per ha, respectively.

The isolated and characterized species of the present invention, *Steinernema scarabaei*, is deposited at the American Type Culture Collection (ATCC), accession No. PTA-6988.

EXAMPLES

Example I

Nematode Extraction and Culture.

A previously unknown nematode of the genus *Steinernema* (suggested taxonomic name: *Steinernema scarabaei*) (*Steinernema scarabaei* n. sp. (Rhabditida: Steinernematidae), a natural pathogen of scarab beetle larvae (Coleoptera: Scarabaeidae)) was isolated from infected Japanese beetle and oriental beetle larvae collected from turfgrass plots at the Rutgers Research Farm in Adelphia, N.J., during epizootics of this nematode in populations of these scarab species. Additional nematodes were isolated by keeping field-collected Japanese beetle larvae and oriental beetle larvae at room temperature (22-26° C.) in 30-ml plastic cups filled with soil collected from the turfgrass plots. Infected larvae were collected from the cups 7-14 days after exposure to the soil samples. Infected larvae from the field collections or from the cup exposure were transferred to White traps (White, Science, 665:302-303, 1929) to collect the emerging progeny infective juveniles.

The *Steinernema scarabaei* nematodes were cultured in the laboratory in Japanese beetle and oriental beetle larvae. Following harvest the infective juveniles were suspended in 50 ml of water and stored in 275-ml canted neck Corning tissue culture flasks at 110° C. Nematodes were used for experiments within 1 month of harvesting.

Larvae of Japanese beetle and oriental beetle were collected from infested turfgrass areas in Adelphia, N.J., and stored in pasteurized soil individually in the wells of 24-well tissue culture plates at 10° C. Before use in experiments or for nematode rearing the larvae were kept at room temperature for 2-3 days to allow for the expression of infection signs if they had previously been infected with nematodes. Any scarab larvae used for rearing and any experiments described below were in the third larval stage.

*Steinernema scarabaei* was also reared in the late instar larvae of the greater wax moth, *Galleria mellonella*. Wax moth larvae are a standard laboratory host for most entomopathogenic nematode species, and are easily available from commercial fish bait producers. While the percentage of cadavers producing progeny nematodes was somewhat less consistent in wax moth larvae (50-90%) than in oriental and Japanese beetle larvae (80-90%), there was no significant difference in number of progeny emerging per IJ-producing cadaver. The pathogenicity against oriental beetle $3^{rd}$ instars of IJs produced in wax moth larvae also did not differ significantly from those produced in oriental beetle larvae.

Example II

Infectivity Compared to Other Nematode Species/Isolates.

Overall, *Steinernema scarabaei* was the most pathogenic nematode species/isolate (Table 1). The infectivity of *Steinernema scarabaei* was determined in larvae of 5 scarab species: Japanese beetle, oriental beetle, Asiatic garden beetle, European chafer, and northern masked chafer. For comparison, 3-5 other nematode species/isolates were included in the test: *S. glaseri* (NC strain), *H. bacteriophora* (TF strain), *H. bacteriophora* (R isolate, recently isolated with wax moth larvae from soil in Connecticut), *H. bacteriophora* (HO isolate, recently isolated from field-infected larvae of oriental beetle and northern masked chafer in Adelphia, N.J.), and *Heterorhabditis* sp. (a potentially new species from Korea). The larvae were kept individually in 30-ml plastic cups filled with 25 g of moist (12% w/w; −7 kPa water potential) sandy loam soil and perennial ryegrass as food. 400 infective juveniles were added in 0.5 ml water and the cups checked for larval mortality at 7 and 14 days after treatment (DAT). The experiments were conducted at room temperature (22-26° C.). Each treatment had 4 replicates with 10 larvae each. The percentage mortality data were arcsine square root transformed and subjected to an analysis of variance by scarab species using the General Linear Model (GLM) procedure software of SAS (SAS Institute, Cary, N.C., 1996). Means were separated using Tukey's test (P<0.05).

The Japanese beetle was the most nematode-susceptible scarab species with $\geq 60/\geq 88\%$ mortality at 7/14 DAT in all nematode treatments. At 7 DAT, *Steinernema scarabaei* and *H. bacteriophora* (HO) caused significantly higher mortality than any other nematode (F=87.1; df=6, 21; P<0.001), but at 14 DAT, mortality had increased in all nematode species so that only one isolate (*H. bacteriophora* R) had caused significantly less mortality than *Steinernema scarabaei* (F=36.9; df=6, 21; P<0.001). While the 7 DAT data indicate the superiority of *Steinernema scarabaei*, clearer differences could be expected at lower nematode application rates. In the less nematode-susceptible oriental beetle, Asiatic garden beetle, and European chafer, *Steinernema scarabaei* outperformed any other nematode isolate with 80-100/100% mortality at 7/14 DAT compared to ≦43/≦55% at 7/14 DAT for any other nematode isolate (oriental beetle and Asiatic garden beetle: F≧24.2; df=6, 21; P<0.001. European chafer: F≧75.9; df=4, 15; P<0.001).

Example III

Dose Response of *Steinernema scarabaei* in Japanese Beetle and Oriental Beetle Larvae.

The larvae were kept individually in 30-ml plastic cups filled with 25 g of moist (12% w/w; −7 kPa water potential) sandy loam soil and perennial ryegrass as food. *Steinernema scarabaei* dosages were 0, 6, 13, 20, 25, 50, 100, and 200 IJs/larvae for *P. japonica* and 0, 13, 20, 25, 50, 100, and 200 IJs/larva for *E. orientalis*. Infective juveniles were added in 0.5 ml water and the cups checked for larval mortality at 7 and 14 DAT. Each treatment had 4 replicates with 10 larvae each. The experiment was conducted at room temperature (22-26° C.). The percentage mortality data were arcsine square root transformed and subjected to an analysis of variance by scarab species using the General Linear Model (GLM) procedure software of SAS (SAS Institute, Cary, N.C., 1996). Means were separated using Tukey's test (P<0.05). The dosage mortality data for *P. japonica* and *E. orientalis* were also analyzed using probit analysis.

*E. orientalis* mortality by *Steinernema scarabaei* increased significantly in a dose response at 7 and 14 DAT (F≧30.4; df=5, 18; P<0.001) (Table 2). At a dose of 50-200 IJs/larva, mortality was 95-100% at 14 DAT. Using the dosage range of 13 to 50 IJs, the LC50 (95% fiducial limits) at 14 DAT was 17.9 (15.6-20.2) IJs/larva. The LC90 (95% fiducial limits) at 14 DAT was 35.2 (29.6-48.0) IJs/larva. *P. japonica* mortality also increased significantly with dosage at 7 and 14 DAT (F≧32.2; df=6, 21; P<0.001) (Table 2). At a dose of 20-200 IJs/larva, mortality was 90-100% at 14 DAT. Using the dosage range of 6 to 50 IJs, the LC50 (95% fiducial limits) at 14 DAT was 10.9 (5.8-15.5) IJs/larva. The LC90 (95% fiducial limits) at 14 DAT was 22.3 (15.6-67.8) IJs/larva. Based on the lack of overlap of LC50 fiducial limits at 7 DAT (data not shown) and 14 DAT, *Steinernema scarabaei* was more pathogenic to *P. japonica* than *E. orientalis*.

Example IV

Effect of Nematode Dosage on *Steinernema scarabaei* Infectivity and Development. All Dosages of *Steinernema scarabaei* Caused High Oriental Beetle Mortality (85-98%) (Table 3).

*E. orientalis* larvae were kept individually in 30-ml plastic cups filled with 18 g of moist (12% w/w; −7 kPa water potential) sandy loam soil and perennial ryegrass as food. The experiment was conducted at room temperature (22-26° C.). 0, 25, 38, 50, 100, or 200 *Steinernema scarabaei* infective juveniles were added in 0.4 ml water and the cups checked daily for larval mortality until 14 DAT. There were 40 larvae per dosage. Larvae from one half of the replicates that died were dissected 2 days after death to count the number of nematodes established in the cadavers. Larvae from the other half of the replicates that died were placed individually on White traps to determine the first day of emergence and the total number of nematode progeny emerging from the cadavers. The number of progeny for each grub cadaver was determined by counting four subsamples under a dissecting microscope. For the determination of grub mortality, groups of 10 cups were considered a replicate. For the determination of progeny emergence, individual grubs were considered replicates; grubs that produced no progeny were not included. The percentage mortality data were arcsine square root transformed before analysis. Data for percentage mortality, day of host death (in DAT), number of nematodes established per cadaver, first day of emergence of nematode progeny from cadavers, and total number of nematode progeny per cadaver were subjected to an analysis of variance using the General Linear Model (GLM) procedure software of SAS (SAS Institute, Cary, N.C., 1996). Means were separated using Tukey's test (P<0.05).

Mortality in the control was 7.5%. All dosages of *Steinernema scarabaei* caused high oriental beetle mortality (85-98%) without significant differences among dosages (Table 3). The time until host death occurred decreased with nematode dosage (F=5.4; df=4, 184; P<0.001) in a linear fashion (y=5.39-9.24x; $r^2$=0.83). Nematode establishment increased with nematode dosage (F=63.5; df=4, 77; P<0.001) in a linear fashion (y=−1.99+0.47x; $r^2$=0.99) with mean establishment rates of 41-46%. Timing of first nematode progeny emergence from host cadavers was not affected by dosage (P=0.48). Progeny numbers were lower at 100 infective juveniles per host than at 25 infective juveniles per host (F=2.6; df=4, 78; P=0.04) but there was no relationship between progeny number and dosage (y=24.05-0.02x; $r^2$=0.1).

Example V

The efficacy of *Steinernema scarabaei* against 5 scarab species (Japanese beetle, oriental beetle, Asiatic garden beetle, European chafer, northern masked chafer) was determined under greenhouse conditions in comparison to various other nematode species/isolates. Japanese beetle larvae were the most nematode susceptible species and even at the rate of $0.3125 \times 10^9$ infective juveniles per ha, *Steinernema scarabaei* provided 90% control. In the less nematode-susceptible oriental beetle larvae *Steinernema scarabaei* caused a 2-4 times higher mortality than any other nematode isolate.

One-liter square pots (10×10×10 cm) filled with soil to a height of 9 cm were seeded with perennial ryegrass and watered every 2-3 days until the end of the experiment. The grass was allowed to grow for 4 weeks before introduction of 5 larvae per pot. The larvae were placed on the grass 3 days before the start of an experiment. Larvae that had not entered into the soil within 24 h were replaced. The temperature in the pots at a 5-cm soil depth averaged 23.3±1.5° C. Treatments were applied in 50 ml of water. Pots were arranged in a completely randomized design.

Against Japanese beetle larvae treatments included *Steinernema scarabaei* at 1.25, 0.3125, and $0.156 \times 10^9$ IJs/ha, and *H. bacteriophora* TF at 1.25 and $0.3125 \times 10^9$ IJs/ha. Against oriental beetle larvae treatments included *Steinernema scarabaei* at 1.25, 0.625, 0.3125, and $0.156 \times 10^9$ infective juveniles per ha, and *H. bacteriophora* TF, *H. bacteriophora* HO, *H. bacteriophora* R, *S. glaseri* NC, *S. glaseri* NJ43, and *Heterorhabditis* spec. each at $1.25 \times 10^9$ IJs/ha. Against Asiatic garden beetle larvae treatments included *Steinernema scarabaei* at 2.5 and $1.25 \times 10^9$ infective juveniles per ha. Against European chafer larvae *Steinernema scarabaei* was applied at $1.25 \times 10^9$ IJs/ha. Against northern masked chafer larvae treatments included *Steinernema scarabaei* at 2.5, 1.25, 0.625, and 0.3125×10$^9$ infective juveniles per ha, and *H. bacteriophora* TF, *H. bacteriophora* HO, and *S. glaseri* NJ43 each at 1.25×10$^9$ infective juveniles per ha. There were 7-20 pots per treatment. The number of surviving larvae was determined at 14 DAT and the data subjected to analysis of variance by scarab species using the General Linear Model (GLM) procedure software of SAS (SAS Institute, Cary, N.C., 1996). Means were separated using Tukey's test (P<0.05).

The results were similar to the laboratory observations (Example II) with respect to ranking of nematode efficacy and susceptibility of scarab species (Table 4). Japanese beetle larvae were the most nematode susceptible species and even at the rate of 0.3125×10$^9$ infective juveniles per ha, *Steinernema scarabaei* provided 90% control. Only at the lowest *Steinernema scarabaei* rate did control drop significantly (F=54.68; df=5, 51; P<0.001). In the less nematode-susceptible oriental beetle larvae *Steinernema scarabaei* caused a 2-4 times higher mortality than any other nematode isolate (F=53.1; df=10, 139; P<0.001). Even at ⅛ the application rate, *Steinernema scarabaei* still caused a higher mortality than any other nematode isolate. In Asiatic garden beetle (F=121.2; df=2, 29; P<0.001) and European chafer larvae (F=529.4; df=1, 14; P<0.001), *Steinernema scarabaei* provided very good and complete control, respectively.

Example VI

Field Efficacy Against Japanese and Oriental Beetle Larvae.

Against Japanese beetle larvae, *Steinernema scarabaei* provided complete control (100%) within 14 days even at the lower application rate (Table 5). Oriental beetle larvae were generally less susceptible to nematode infection, but *Steinernema scarabaei* provided excellent control (80-93%) even at 14 DAT at the lower application rate (F≧17.3; df=3, 8; P<0.001). The high infection rate of Japanese beetle and oriental beetle larvae by *Steinernema scarabaei* indicates that this species can not only provide excellent short term control of scarab larvae but also has a high potential for long-term suppression due to efficient reproduction in its hosts.

A field experiment was conducted at the Rutgers University Research Farm in Adelphia (Freehold, N.J.) in an area planted with perennial ryegrass and maintained using standard management procedures. The soil was a sandy loam (67% sand, 19 silt, 14% clay, 2% organic matter, pH 6.7). Preapplication sampling showed that the site had no resident white grub or entomopathogenic nematode populations. Treatments were applied on May 17, 2001 at 6 μm (soil temperature at 5 cm depth 19° C.; air temperature 18° C.; cloudy) in 12.5 liter of water per m$^2$ (=12.5 mm) using a watering can. Because the soil was already moist before application no additional irrigation was applied. Plots measured 60×60 cm with 1 m buffer between plots. Each plot was surrounded by plastic edging material pushed 10 cm into the ground to restrict lateral movement of larvae. There were 3 replicate plots per treatment arranged in a randomized complete block design. 20 Japanese and 20 oriental beetle larvae were released into each plot. Larvae that did not dig into the soil within 30 min were replaced.

Treatments were *Steinernema scarabaei* and *H. bacteriophora* TF each at 2.5 and 10$^9$ infective juveniles per ha. Controls received only water. The treatments were evaluated at 14 and 21 DAT by taking five 10 cm diam turf plugs (with a standard size golf hole cutter) to a depth of 7.5 cm and counting the number of surviving grubs and nematode-infected grubs for each species. Percentage control was calculated for each data point relative to the average number of surviving larvae recovered from the control plots. Percentage infection was calculated for each plot by dividing the number of larvae infected by the treatment nematode species by the total number of larvae, dead and alive, recovered. After arcsine square root transformation, the data were subjected to an analysis of variance by scarab species using the General Linear Model (GLM) or t-test (if only 2 means were compared) procedure software of SAS (SAS Institute, Cary, N.C., 1996). After GLM analysis means were separated using Tukey's test (P=0.05).

During the experimental period, soil temperature at 5 cm depth was 18.9±1.0° C. and there was a total of 81 mm of rainfall and overhead irrigation. In the control plots the following number of live larvae were recovered in 5 turf/soil cores: 5.0±1.2 and 5.0±1.2 Japanese beetle larvae at 14 and 21 DAT, respectively, and 5.0±1.2 and 5.0±0.6 oriental beetle larvae at 14 and 21 DAT, respectively. Against Japanese beetle larvae, *Steinernema scarabaei* provided complete control (100%) within 14 days even at the lower application rate (Table 5). Oriental beetle larvae were generally less susceptible to nematode infection, but *Steinernema scarabaei* provided excellent control (80-93%) even at 14 DAT at the lower application rate (F≧17.3; df=3, 8; P<0.001). *H. bacteriophora* TF, on the other hand, provided no oriental beetle control at 14 DAT and only 53% even at the higher application rate and 21 DAT.

Example VII

Field Efficacy Against Asiatic Garden Beetle Larvae.

A field experiment was conducted at the Rutgers University Research Farm in Adelphia (Freehold, N.J.) in an area planted with perennial ryegrass and maintained using standard management procedures. The soil was a sandy loam (67% sand, 19 silt, 14% clay, 2% organic matter, pH 6.7). Preapplication sampling showed that the site had no resident white grub or entomopathogenic nematode populations. Treatments were applied on Jun. 5, 2001 at 11 am (soil temperature at 5 cm depth 20° C.; air temperature 21° C.; sunny) in 12.5 liter of water per m$^2$ (=12.5 mm) using a watering can. Because the soil was already moist before application no additional irrigation was applied. Plots measured 30×30 cm with 1 m buffer between plots. Each plot was surrounded by plastic edging material pushed 10 cm into the ground. There were 7 replicate plots per treatment arranged in a randomized complete block design. 19 Asiatic garden beetle larvae were released into each plot. Larvae that did not dig into the soil within 30 min were replaced. Treatments were *Steinernema scarabaei* at 2.5 and 10$^9$ infective juveniles per ha and *H. bacteriophora* TF at 2.5×10$^9$ infective juveniles per ha. The treatments were evaluated at 14 DAT by going through the soil of each plot to a depth of 10 cm and counting the number of surviving grubs. Percentage control was calculated for each data point relative to the average number of surviving larvae recovered from the control plots. After arcsine square root transformation, the data were subjected to an analysis of variance using the General Linear Model (GLM) procedure software of SAS (SAS Institute, Cary, N.C., 1996) and means were separated using Tukey's test (P<0.05).

During the experimental period, soil temperature at 5 cm depth was 20.3±1.1° C. and there was a total of 85 mm of rainfall and overhead irrigation. In the control plots, 11.9±1.1 live Asiatic garden beetle larvae were recovered at 14 DAT. *Steinernema scarabaei* provided good control at the higher application rate (Table 7). Control at the lower *Steinernema* spec. rate was not significantly different from the control at the higher rate. Control by *H. bacteriophora* TF, however, was not acceptable and was significantly lower (F=6.0; df=2, 18; P<0.01) than in both *Steinernema scarabaei* treatments.

Example VIII

Field Efficacy Against Northern Masked Chafer Larvae.

A field experiment was conducted at the Rutgers University Research Farm in Adelphia (Freehold, N.J.) in an area planted with perennial ryegrass and maintained using standard management procedures. The soil was a sandy loam (67% sand, 19 silt, 14% clay, 2% organic matter, pH 6.7). Preapplication sampling showed that the site had no resident white grub or entomopathogenic nematode populations. Treatments were applied on Sep. 25, 2001 at 3 μm (soil temperature at 5 cm depth 23° C.; air temperature 22° C.; sunny) in 12.5 liter of water per m² (=12.5 mm) using a watering can. Because the soil was already moist before application no additional irrigation was applied. 12 *C. borealis* larvae were released into each microplot (0.05 ml surrounded by PVC pipe sections pushed 10 cm into the ground to restrict lateral movement of larvae). There were 8 replicate plots per treatment arranged in a randomized complete block design. Treatments were *Steinernema scarabaei* at $2.5 \times 10^9$ IJs/ha and $10^9$ IJs/ha and *H. bacteriophora* (TF strain) at $2.5 \times 10^9$ IJs/ha and $10^9$ IJs/ha. Larval survival was determined at 21 DAT by searching through the soil in the microplots to a depth of 12.5 cm. Percentage control was calculated for each data point relative to the average number of surviving larvae recovered from the control plots. After arcsine square root transformation, the data were subjected to an analysis of variance using the General Linear Model (GLM) procedure software of SAS (SAS Institute, Cary, N.C., 1996) and means were separated using Tukey's test (P<0.05).

During the experiment, air temperatures averaged 15.3° C. and rainfall totaled 38 mm. No additional overhead irrigation was supplied. An average of 8.0±0.6 (range 6-10) *C. borealis* larvae were recovered from the control plots. Number of *C. borealis* larvae recovered varied significantly among treatments (F=12.6; df=9, 20; P<0.001) (Table 8). The highest *Steinernema scarabaei* rate provided significantly higher control (84%) than the lower *Steinernema scarabaei* rate (58%), which in turn provided significantly higher control than the higher (20%) and lower (6%) *H. bacteriophora* (TF strain) rate.

Example IX

Synergistic Interaction of *Steinernema scarabaei* and the Neonicotinoid Insecticide Imidacloprid. Combination of *Steinernema scarabaei* with Imidacloprid Increased the Mortality Caused by *Steinernema scarabaei* in *C. borealis* Larvae and *E. orientalis* Larvae.

A greenhouse pot experiment was conducted to determine whether the application rates of *Steinernema scarabaei* against a susceptible (Oriental beetle) and a less susceptible (northern masked chafer) scarab species could be further decreased by combining it with the neonicotinoid insecticide imidacloprid. Imidacloprid has been shown to synergize with various other entomopathogenic nematode species against scarab larvae (Koppenhöfer & Kaya, Journal of Economic Entomology, 91:618-623,1998; Koppenhöfer et al., Biological Control, 19:245-251, 2000). One-liter square pots (10× 10×10 cm) filled with soil to a height of 9 cm were seeded with perennial ryegrass and watered every 2-3 days until the end of the experiment. The grass was allowed to grow for 4 weeks before introduction of 5 larvae per pot. The larvae were placed on the grass 3 d before the start of an experiment. Larvae that had not entered into the soil within 24 h were replaced. The temperature in the pots at a 5-cm soil depth averaged 23.1±1.3° C. Treatments were applied in 50 ml of water. Controls received water only. Pots were arranged in a completely randomized design.

Treatments were based on previous observations with single control agents against the selected scarab species. Treatments consisted of one rate of imidacloprid (200 g ai/ha; recommended field rate for scarab control in turfgrass is 330-400 g ai/ha), *Steinernema scarabaei* at 0.3125 infective juveniles per ha (both scarab species) or at 0.15625 infective juveniles per ha (only oriental beetle) (recommended field rate for most nematodes against white grubs is 2.5 to $5.0 \times 10^9$ infective juveniles per ha), and the combination of imidacloprid with each *Steinernema scarabaei* rate. There were 10-20 replicate pots per treatment. The pots were destructively sampled at 14 DAT and the number of surviving larvae determined. The data were subjected to an analysis of variance by scarab species using the General Linear Model (GLM) procedure software of SAS (SAS Institute, Cary, N.C., 1996). Means were separated using Tukey's test (P<0.05).

Synergistic, additive, or antagonistic interactions between agents in the combination treatments were determined using a $\chi^2$ test (Finney, Probit Analysis, Cambridge University Press, London, 1964; McVay et al., Journal of Invertebrate Pathology, 29:367-372, 1977; Koppenhöfer & Kaya, Journal of Economic Entomology, 91:618-623,1998). Grub mortality was calculated by subtracting the number of surviving grubs from the number of grubs released for each replicate and correcting for control mortality (Abbott, Journal of Economic Entomology, 18:265-267, 1925). The expected additive proportional mortality ME for the nematode-imidacloprid combinations was calculated by $M_E = M_N + M_I(1-M_N)$ where $M_N$ and $M_I$ are the observed proportional mortalities caused by nematodes and imidacloprid alone, respectively. Results from a $\chi^2$ test, $\chi^2 = (M_{NI}-M_E)^2/M_E$, where $M_{NI}$ is the observed mortality for the nematode-imidacloprid combinations, were compared to the $\chi^2$ table value for 1 df. If the calculated $\chi^2$ value exceeded the table value, a non-additive effect between the two agents was suspected. If the difference $M_{NI}-M_E$ had a positive/negative value, a significant interaction was then considered synergistic/antagonistic.

Combination of *Steinernema scarabaei* with imidacloprid significantly increased the mortality caused by *Steinernema scarabaei* in *C. borealis* larvae (F=52.6; df=3, 52; P<0.001) and by both *Steinernema scarabaei* application rates in *E. orientalis* larvae (F=102.8; df=5, 91; P<0.001) compared to the respective single agent treatments (Table 9). The interactions were synergistic in all combinations tested ($\chi^2 \geq 3.9$; df=1; P<0.04). Imidacloprid alone did not cause significant mortality.

Example X

*Steinernema scarabaei* Taxonomoic Description—Female

Cuticle smooth under light microscopy, but with fine transverse striae visible under SEM. Lateral field and phasmids inconspicuous. Head truncated to slightly round, continuous with the body. Six lips united but tips distinct, and with one labial papilla each located at posterior ⅓ of metacorpus, just anterior to nerve-ring. Ovaries opposed, reflexed in dorsal position; oviduct well developed; glandular spermatheca and uterus in ventral position. Vagina short, with muscular walls. Vulva located near middle of body. First and second generation females with vulval lips slightly protruding. First generation female with conoid tail, with mucro and one caudal papilla located at the base of the mucro. Second generation female with blunt-conoid tail, without mucro, without caudal papilla. First generation female without post-anal swelling. Second generation female with post-anal swelling.

Example XI

*Steinernema scarabaei* Taxonomoic Description—Male

Cuticle, lip region, stoma and oesophageal region as in female. Body curved posteriorly, "J"-shaped when heat-killed. Single reflexed testis, consisting of germinal growth zone leading to seminal vesicle. Vas deferens with inconspicuous walls. Spicules paired, symmetrical, curved, with ocre-brown coloration. Manubrium romboid. Lamina with rostrum (retinaculum) and 2 internal ribs. Velum present. Gubernaculum arcuate, about ¾ length of spicules. First generation male with conoid and mucronated tail. Second generation males with rounded tail without mucro. There are 23-25 genital papillae (11-12 pairs and one single) arranged as follows: 6 precloacal subventral pairs, one precloacal lateral pair; one single ventral precloacal papilla (located between precloacal pairs 5 and 6); one pair adcloacal (or postcloacal in some specimens); one pair postcloacal subventral, one postcloacal subdorsal pair, one postcloacal terminal pair, near tail tip. An additional pair of papillae (40% of the specimens examined), at the base of the cloacal cone may be present in first generation males.

Example XI

*Steinernema scarabaei* Taxonomoic Description—Third Stage Infective Juvenile

Body slender, tapering regularly from base of oesophagus to anterior end and from anus to terminus. Lip region smooth; mouth closed. Cuticle with transverse striae; lateral field distinct with 8 longitudinal ridges in mid-body region. Oesophagus long, narrow. Nerve-ring located at level of isthmus. Excretory pore located about the middle of oesophagus. Basal bulb valvate. Cardia present. Anterior portion of intestine with dorsally displaced pouch containing symbiotic bacterium. Lumen of intestine narrow; rectum long; anus distinct. Genital primordium evident. Tail conoid with pointed terminus.

Tables

TABLE 1

Effect of nematode species/isolate on mortality of 5 scarab species larvae in 30-ml cups filled with soil and grass after exposure to 400 infective juvenile nematodes per cup for 7 and 14 days.

| Nematode | *P. japonica* | *E. orientalis* | *M. castanea* | *C. borealis* | *R. majalis* |
| --- | --- | --- | --- | --- | --- |
| 7 DAT | | | | | |
| *Steinernema scarabaei* | 98 ± 2 a | 96 ± 3 a | 80 ± 7 a | 35 ± 5 bc | 100 ± 0 a |
| *S. glaseri* NC | 60 ± 7 c | 35 ± 3 b | 20 ± 7 bc | 10 ± 7 cd | 40 ± 7 b |
| *H. bacteriophora* TF | 85 ± 3 b | 13 ± 5 cd | 3 ± 3 c | 30 ± 6 bc | 8 ± 5 c |
| *H. bacteriophora* R | 75 ± 6 bc | 13 ± 3 cd | 5 ± 3 c | 40 ± 0 ab | 35 ± 6 b |
| *H. bacteriophora* HO | 100 ± 0 a | 23 ± 2 bc | 43 ± 5 b | 75 ± 10 a | — |
| *Heterorhabditis* spec. | 87 ± 2 b | 15 ± 3 bcd | 33 ± 3 b | 43 ± 9 b | — |
| Control | 3 ± 3 d | 3 ± 3 d | 3 ± 3 c | 3 ± 3 d | 3 ± 3 c |
| 14 DAT | | | | | |
| *Steinernema scarabaei* | 100 ± 0 a | 98 ± 3 a | 100 ± 0 a | 45 ± 3 bc | 100 ± 0 a |
| *S. glaseri* NC | 88 ± 7 ab | 45 ± 3 b | 23 ± 5 c | 20 ± 4 c | 43 ± 5 bc |
| *H. bacteriophora* TF | 93 ± 3 ab | 18 ± 5 c | 5 ± 3 d | 45 ± 3 bc | 25 ± 6 c |
| *H. bacteriophora* R | 80 ± 4 b | 20 ± 4 c | 5 ± 3 d | 63 ± 8 b | 55 ± 6 b |
| *H. bacteriophora* HO | 100 ± 0 a | 30 ± 4 bc | 55 ± 6 b | 85 ± 5 a | NA |
| *Heterorhabditis* spec. | 90 ± 0 ab | 25 ± 3 bc | 50 ± 7 bc | 60 ± 7 b | NA |
| Control | 8 ± 3 c | 3 ± 3 d | 3 ± 3 d | 5 ± 3 d | 3 ± 3 d |

[1]Means followed by same letter within columns are not significantly different ($P < 0.05$, Tukey).

TABLE 2

Dose response of *Steinernema scarabaei* against *Popillia japonica* and *Exomala orientalis* $3^{rd}$ instars in 30-ml plastic cups filled with 25 g moist soil and grass 7 and 14 days after treatment (DAT).

| | *P. japonica* | | *E. orientalis* | |
| --- | --- | --- | --- | --- |
| No. Ijs | 7 DAT | 14 DAT | 7 DAT | 14 DAT |
| 0 | 0.0 ± 0.0 | 0.0 ± 0.0 | 0.0 ± 0.0 | 0.0 ± 0.0 |
| 6 | 15.0 ± 2.9 c | 22.5 ± 4.8 c | — | — |
| 13 | 40.0 ± 4.1 b | 45.0 ± 2.9 b | 25.0 ± 2.9 c | 30.0 ± 4.1 d |
| 20 | 85.0 ± 2.9 a | 90.0 ± 4.1 a | 50.0 ± 4.1 bc | 52.5 ± 4.8 c |
| 25 | 90.0 ± 4.1 a | 95.0 ± 2.9 a | 57.5 ± 4.8 b | 70.0 ± 4.1 b |
| 50 | 95.0 ± 5.0 a | 100.0 ± 0.0 a | 97.5 ± 2.5 a | 100.0 ± 0.0 a |
| 100 | 97.5 ± 2.5 a | 97.5 ± 2.5 a | 97.5 ± 2.5 a | 97.5 ± 2.5 a |
| 200 | 97.5 ± 2.5 a | 97.5 ± 2.5 a | 87.5 ± 5.0 a | 95.0 ± 5.0 a |

[1]Means followed by same letter within columns are not significantly different ($P < 0.05$, Tukey).

TABLE 3

Effect of *Steinernema scarabaei* dosage on *Exomala orientalis* larvae mortality, time until host death, number of nematodes established per host cadaver, 1$^{st}$ day of nematode progeny emergence from host cadaver, and number of nematode progeny per cadaver.

| No. IJs | % mortality[1] | Speed of kill (DAT) | Nematode establishment | 1$^{st}$ day of emergence | No. progeny (×1000) |
|---|---|---|---|---|---|
| 25  | 85 ± 7 a  | 5.5 ± 0.4 a   | 10.6 ± 1.0 c | 19.0 ± 1.1 a | 28.5 ± 3.4 a  |
| 38  | 98 ± 2 a  | 5.1 ± 0.3 ab  | 16.1 ± 2.0 c | 18.8 ± 0.7 a | 20.3 ± 2.3 ab |
| 50  | 95 ± 5 a  | 4.7 ± 0.3 abc | 20.4 ± 2.5 c | 17.8 ± 0.7 a | 24.7 ± 3.0 ab |
| 100 | 93 ± 5 a  | 4.1 ± 0.3 bc  | 43.6 ± 4.4 b | 18.7 ± 1.0 a | 15.2 ± 2.5 b  |
| 200 | 98 ± 2 a  | 3.7 ± 0.2 c   | 92.0 ± 6.9 a | 17.2 ± 0.5 a | 22.5 ± 2.9 ab |

[1]Control mortality 7.5%.
[2]Means followed by same letter within columns are not significantly different ($P < 0.05$, Tukey).

TABLE 4

Effect of nematode species and application rate on percentage control (±SEM) of 5 scarab species larvae in pots with grass in the greenhouse at 14 days after treatment.

| Nematode | Rate[1] | *P. japonica* | *E. orientalis* | *M. castanea* | *C. borealis* | *R. majalis* |
|---|---|---|---|---|---|---|
| *Steinernema scarabaei* | 25.0 | — | — | 94 ± 3 a | 66 ± 7 a | — |
| "  | 12.5 | 97 ± 3 a[2] | 96 ± 2 a  | 80 ± 7 a | 69 ± 5 a | 100 ± 0 a |
| "  | 6.3  | —          | 94 ± 3 a  | —        | 48 ± 7 ab | — |
| "  | 3.1  | 90 ± 3 a   | 76 ± 4 ab | —        | 38 ± 5 b  | — |
| "  | 1.56 | 64 ± 5 b   | 68 ± 7 bc | —        | —         | — |
| *S. glaseri* NC | 12.5 | — | 16 ± 5 ef | — | — | — |
| *S. glaseri* NJ43 | 12.5 | — | 32 ± 7 de | — | 6 ± 4 dc | — |
| *H. bacteriophora* TF | 12.5 | 94 ± 4 a | 24 ± 3 ef | — | 49 ± 4 ab | — |
| " | 3.1 | 82 ± 5 ab | — | — | — | — |
| *H. bacteriophora* R | 12.5 | — | 34 ± 5 de | — | — | — |
| *H. bacteriophora* HO | 12.5 | — | 47 ± 4 cd | — | 62 ± 8 ab | — |
| *Heterorhabditis* sp. | 12.5 | — | 24 ± 6 | — | — | — |
| Control | 0 | 14 ± 5 c | 9 ± 3 f | 7 ± 3 b | 2 ± 1 c | 26 ± 4 b |

[1]Rate in 10$^9$ infective juvenile nematodes per ha (2.5 × 10$^9$ = standard field rate).
[2]Means followed by same letter within columns are not significantly different ($P < 0.05$, Tukey).

TABLE 5

Effect of nematode species and rate on percentage control (±SEM) of *P. japonica* and *E. orientalis* larvae in a turfgrass area at 14 and 21 days after treatment (DAT).

| | | *P. japonica* | | *E. orientalis* | |
|---|---|---|---|---|---|
| Nematode | Rate[1] | 14 DAT | 21 DAT | 14 DAT | 21 DAT |
| *Steinernema scarabaei* | 2.5 | 100 ± 0 a[2] | 100 ± 0 a | 93 ± 7 a | 93 ± 7 a |
| *Steinernema scarabaei* | 1.0 | 100 ± 0 a | 100 ± 0 a | 80 ± 0 a | 87 ± 7 ab |
| *H. bacteriophora* TF | 2.5 | 73 ± 7 ab | 93 ± 7 a | 7 ± 7 b | 53 ± 13 bc |
| *H. bacteriophora* TF | 1.0 | 33 ± 13 b | 40 ± 12 b | 0 ± 12 b | 40 ± 12 c |

[1]rate in 10$^9$ infective juvenile nematodes per ha (2.5 × 10$^9$ = standard field rate).
[2]Means followed by same letter within columns are not significantly different ($P < 0.05$, Tukey).

TABLE 6

Percentage infection[1] of *P. japonica* and *E. orientalis* larvae after treatment with different rates of *Steinernema scarabaei* and *Heterorhabditis bacteriophora* TF in a turfgrass area.

| | | % *P. japonica* control | | % *E. orientalis* control | |
|---|---|---|---|---|---|
| Nematode | Rate[2] | 14 DAT | 21 DAT | 14 DAT | 21 DAT |
| *Steinernema scarabaei* | 2.5 | 100 ± 0 a[3] | —[4] | 94 ± 6 a | — |
| *Steinernema scarabaei* | 1.0 | 100 ± 0 a | — | 79 ± 2 b | — |
| *H. bacteriophora* TF | 2.5 | 79 ± 2 b | 67 ± 33 | 0 ± 0 | 0 ± 0 |
| *H. bacteriophora* TF | 1.0 | 42 ± 9 c | 28 ± 14 | 0 ± 0 | 0 ± 0 |

[1]Infection with treatment nematode species; no infections with non-treatment nematode species were found.
[2]Rate in 10$^9$ infective juvenile nematodes per ha (2.5 × 10$^9$ = standard field rate).
[3]Means followed by same letter within columns are not significantly different ($P < 0.05$, Tukey or t-test).
[4]Because of advanced stage of infection only few cadavers could be recovered at 21 DAT.

TABLE 7

Effect of nematode species and rate on percentage control
(±SEM) of *M. castanea* larvae in a turfgrass area at 14
days after treatment.

| Nematode | Rate[1] | 1st trial % control |
|---|---|---|
| Steinernema scarabaei | 2.5 | 71 ± 7 a[2] |
| Steinernema scarabaei | 1.0 | 60 ± 6 a |
| H. bacteriophora TF | 2.5 | 33 ± 11 b |

[1]rate in $10^9$ infective juvenile nematodes per ha (2.5 × $10^9$ = standard field rate).
[2]Means followed by same letter within columns are not significantly different (P < 0.05, Tukey).

TABLE 8

Effect of nematode species and rate on percentage control
(±SEM) of *C. borealis* larvae in a turfgrass area at 21 days
after treatment.

| Nematode | Rate[1] | 1st trial % control |
|---|---|---|
| Steinernema scarabaei | 2.5 | 84 ± 6 a[2] |
| Steinernema scarabaei | 1.0 | 58 ± 10 b |
| H. bacteriophora TF | 2.5 | 20 ± 6 c |
| H. bacteriophora TF | 1.0 | 6 ± 9 c |

[1]rate in $10^9$ infective juvenile nematodes per ha (2.5 × $10^9$ = standard field rate).
[2]Means followed by same letter within columns are not significantly different (P < 0.05, Tukey).

TABLE 9

Effect of combination of *Steinernema scarabaei* with
imidacloprid on control of *Exomala orientalis* and
*Cyclocephala borealis* larvae in a greenhouse pot experiment.

| Treatment | Nematode rate[1] | Imidacloprid rate (g ai/ha) | E. orientalis (% control) | C. borealis (% control) |
|---|---|---|---|---|
| Imidacloprid | 0.0 | 200 | 14 ± 4 d[2] | 6 ± 3 c |
| Steinernema scarabaei | 0.313 | 0 | 76 ± 7 bc | 38 ± 6 b |
| Imidacloprid + Steinernema scarabaei | 0.313 | 200 | 93 ± 3 a*[3] | 62 ± 7 a** |
| Steinernema scarabaei | 0.156 | 0 | 68 ± 7 c | — |
| Imidacloprid + Steinernema scarabaei | 0.156 | 200 | 92 ± 3 ab** | — |
| Control | 0.0 | 0 | 9 ± 4 d | 2 ± 1 c |

[1]rate in $10^9$ infective juvenile nematodes per ha (2.5 × $10^9$ = standard field rate).
[2]Means followed by same letter within columns are not significantly different (P < 0.05, Tukey).
[3]Asterisks indicates significant synergistic interaction between the combined control agents ($\chi^2$ test; */** indicate P < 0.05/0.01).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. A method of controlling the larvae of at least one species of scarab beetle comprising applying a biopesticide composition to the locus of the larvae to be controlled, wherein the composition comprises an insecticidally effective amount of an isolated entomopathogenic nematode of the species *Steinernema scarabaei* and wherein the composition further comprises imidacloprid.

2. The method of claim 1 wherein the species of scarab beetle is selected from the group consisting of Japanese beetle (*Popillia japonica*), oriental beetle (*Exomala* (*Anomala*) *orientalis*), European chafer (*Rhizotrogus majalis*), Asiatic garden beetle (*Maladera castanea*), masked chafer (*Cyclocephala* spp.), and May/June beetle (*Phyllophaga* spp.).

* * * * *